United States Patent
Liu et al.

(10) Patent No.: US 7,132,526 B2
(45) Date of Patent: Nov. 7, 2006

(54) ISOLATION AND CHARACTERISATION OF AN ANTHER-SPECIFIC PROMOTER (COFS) IN COTTON

(75) Inventors: Jian-Wei Liu, Singapore (SG); Xuebao Li, Singapore (SG); Lin Cai, Singapore (SG); Ninghui Cheng, Singapore (SG)

(73) Assignee: Temasek Life Sciences Laboratory, Singapore (SG)

( * ) Notice: Subject to any disclaimer, the term of this patent is extended or adjusted under 35 U.S.C. 154(b) by 282 days.

(21) Appl. No.: 10/466,521

(22) PCT Filed: Jan. 17, 2001

(86) PCT No.: PCT/SG01/00022

§ 371 (c)(1),
(2), (4) Date: Feb. 17, 2004

(87) PCT Pub. No.: WO02/057470

PCT Pub. Date: Jul. 25, 2002

(65) Prior Publication Data

US 2004/0158892 A1 Aug. 12, 2004

(51) Int. Cl.
*C12N 15/82* (2006.01)
*A01H 5/00* (2006.01)

(52) U.S. Cl. .................... 536/24.1; 800/298

(58) Field of Classification Search .............. 536/24.1; 800/298
See application file for complete search history.

(56) References Cited

FOREIGN PATENT DOCUMENTS

| WO | WO 92/13957 A | 8/1992 |
|----|---------------|--------|
| WO | WO 97/13401 A | 4/1997 |

OTHER PUBLICATIONS

Worrall D. et al. Premature dissolution of the microsporocyte callose wall causes male sterility in transgenic tobacco. Plant Cell. Jul. 1992; 4(7):759-71.*

Essa Project, "*Arabidopsis thaliana* DNA Chromosome 4, BAC Clone T32A16" Database EMBL 'Online!, 1999, Database Accession No. AL078468k, XP-002177464.

Fulda et al., "*B.napus* mRNA for acyl-CoA Synthetase", Plant Mol. Biol., 1997, vol. 33, pp. 911-922, Database Accession No. X94624, XP-002177465.

Galau et al., "Gossypium Hirsutum Lea5-A Late Embryogenesis-Abundant Protein (Lea5-A) Gene, Complete cds", Plant Physiol, 1993, vol. 101, pp. 695-696, Database Accession No. M37697, XP-002177466.

Paul W. et al., "The Isolation and Characterisation of the Tapetum-Specific *Arabidopsis-thaliana* A9 Gene", Plant Molecular Biology, 1992, vol. 19, No. 4, pp. 611-622, XP-001024223.

Rubinelli P. et al., "Identification, Sequence Analysis and Expression Studies of Novel Anther-Specific Genes of *Arabidopsis thaliana*", Plant Molecular Biology, 1998, vol. 37, No. 4, pp. 607-619, XP-002177463.

Scott R. et al., "Patterns of Gene Expression in Developing Anthers of *Brassica-napus*", Plant Molecular Biology, 1991, vol. 17, No. 2, pp. 195-207, XP-001024222.

Zabaleta E. et al., "Promoters of nuclear-encoded respiratory chain Complex I genes from *Arabidopsis thaliana* Contain a Region Essential for Anther/Pollen-Specific Expression", Plant Journal, 1998, vol. 15, No. 1, pp. 49-59, XP-001024221.

* cited by examiner

*Primary Examiner*—Cynthia Collins
(74) *Attorney, Agent, or Firm*—Rothwell, Figg, Ernst & Manbeck pc

(57) ABSTRACT

The present invention relates to an anther-specific cotton gene (CoFS), and active promoter fragments thereof. These promoters show strong anther-specific activity.

2 Claims, 5 Drawing Sheets

FLOWER  FLOWER  ANTHER

SEQUENCE LISTING

<160> NUMBER OF SEQ ID NOS: 3

<210> SEQ ID NO 1
<211> LENGTH: 8367
<212> TYPE: DNA
<213> ORGANISM: Arabidopsis sp.

<400> SEQUENCE: 1

```
cctcacattt aagcggaaaa aaatattaac taattactaa ttactaaggt catgggttgc      60
gcattaaagt tcactgacga ttgtgcaaat gatgttccat agagcttaat tgatgaaatg     120
ggaactcatg acccgcttga agtaactcga cttgtagaac tcatgaagaa gcttatctac     180
ttgaagtttt ggtagcccaa tgaaatactc tcgtaaatct agagttatta gtgtaaaccc     240
taaagggatc aaattgtata aatttaaatc ccttatgact ttcaattgta gatagactct     300
aatctcgatc atggatgtaa ctcaatctat ttgtttgggtt tggggtgatt acttcaattc    360
attccattca tagttgtgaa tatatttgag agtatttacg caaacatttg gtgtgtgcta     420
ttttteettt ggtetttgt tettegttge ceattegtte gagtttgett tegetatatt     480
ttaatgcctt agaaaatttt tgcgagaatt ctcattttgt gagagttaag cgaacttaga     540
attattttt ttaaaatcgc ttaaggctgt atggtctgtg agactaaaat tctagtctcg       600
taacactaat acaatcacaa gtaatttaca ttgttcaagt tcttattcac ataagcggtt     660
ggataaagaa aattaaaaaa aaacaatcgg atataattac aaaaaaataa attgaaatgt     720
gcaataatac aaataataat tattgctaaa ggtaaataaa aatgtaaat aattatcaat      780
gaagtttgaa accttaaatg gtgaagtttg tgtcaactaa tagaagaaaa aataaattat     840
ttatataact ctactaatgt attattttat tttgtaaaat tgatttatttt atattatttc    900
tactaaattg atgtggaatt agtgatatct acttaattaa ctatatataa ttataatgaa     960
tctccgggac tgtgactggt caaagatcat aaagtggtat ccaataaatt taaaatgcac    1020
ttgtaaaata ttagactcat gatggcactg aggcggaggt gaagaggcgg caaagcacat    1080
ggagaagcta tatagaaaat tctttcacga aaaaggcaac tcttggcttg tgtgttggga    1140
attgtgttaa gaactggatt atataaaaac aattatatgg ggaaaggaaa tggtccactg    1200
tcaatagttt actataagca agttggagat ataaaattaa atatatattc agtacatata    1260
cgagtttgag caacaaaatt agagatcttt tttgtcaagt tgatatcttc aattttataa    1320
cgtaaatgtt cttttgaagg caacagtaat gatatatata tatgtagaag aaatttaact    1380
aaaaatagat aattaggctt aatttaatta attcaagtgc aattgttta tcataatata     1440
tattacatta caaggcttga attattcata tttaatttt attattagt taacaaagta      1500
attattggtg caaaaataaa taattatta ccccattatc tatttctta aataaaaaa        1560
tatattatat atgccattta ctctcttaa aaaaatttaa tttacaaata aactaataaa      1620
tttgtatatg atgatttcga atgagggttt taatacagtt atcatgatga tttcaataca    1680
atggttccaa atgaataagg attccactac aacattaaac tcaccataat ggtgattcca    1740
attgagtgtt cctacataat tatcatcata attcttactt ggcaggatac aaaaaataat    1800
aatgggtaag gtaattaaaa attaaaataa ttatcaataa agttttatt atggtgacaa     1860
agtttgataa tcattattaa attattaatt gagtaaaata tttaaatata gtaatgtata    1920
tataatgaat ctccggcgat gttggctgtt caaagatcat aaaatccaat acatttaaaa    1980
tgcagctgta aaatatgatg taaagggcgg ataaagcaca tggagaagcc atatagaaat    2040
```

-continued

```
ttcttccatg aaaaaggcga ctcttagctt gtgtgttggg aattgtgtta agttatatgg    2100
gaaaggaaat attccactgt caatagttta ttataagcaa gtgggagaaa caaaattaaa    2160
tatgttattt tgaaggcaac agtaataata taattataaa ttaaaataac ataatttagg    2220
cttaatttaa ttaatggtaa actataaaaa aaagtcattt ttgtttgctt cagattacat    2280
tttagtcact tatgtttgaa atgttacgtt ttagtcactt acattaccgt tttgttacga    2340
agtggtcact ttaccattaa actctattac ctccctaacg acagtcctac gtggcagtca    2400
aaatgaattt taaatgctaa cttggacgtc cagttgctgg acattttcc ggttcaccta     2460 cagccaccta atacttaggc gctatatatt ttcccaaaat tattctccac atttcactcc    2520
cagagccctc catctatgta gagagctgta agagagaata taaaaaaggg aaagctagct    2580
gaggatcgtt tgattttgga cattttgatg aaacggcctg gaaataattt tgtaatagag    2640
gtagagaaag gtaaagaccc cagcgatgga cagccgtcga tcggtcctgt ttatcgcagt    2700
tcttttgctg ctaatggatt ccctgctccg attcctggaa tggagagttg ctgggacatt    2760
ttccggttcg ttttttagctt tctctttttt actttacgct tcttgcttgg ctgctaagaa    2820
aataaggata ctaggagaag atttgacttc ttctattctt tgctttgatt tcagatggct    2880
ttcgcaatag ttgccatttt ttttgaattt ttacttcccc ttttttaagt tgagtagatt    2940
tttcttctaa tttgttggct ttgttatttt tttatttcgc gacgaggtgg cgatgaaatc    3000
gagaaacgta cttttaagga tcctatgaga aagttatatg caagatcgaa acgcctaata    3060
tttgaaacta ttgaattta acgctcacac agagcaagaa tcgagttact ggtatttcca    3120
ttcttatagc tgaaagattg atggctttca ttcaactcaa tgtaaaactg tgaaataaat    3180
tgtttaatag tagtaattat tttggttttg atgcttatgt gatgtggaga ttaaaatatt    3240
gcctccttat aacttagctg aaccgtagat atgggctgat tgaacttgct aactaactgt    3300
atgacagctc ctatttacga aaaagtaata ttttatttga ggatgatgat ttcgatttca    3360
ttttctcctt gcagtatgtc agttgagaaa tatcctgaca accatatgct tggtcgccga    3420
cagattgtgg atgggaaagt atgttgctgc tgcagtttcc ttttttcttg ttacttttgc    3480
gttctgtttg tagtgcggcc tttgactttt agttcatgta tctaaattga catgctttga    3540
ttgcaggctg gaaaatacgt gtggcaaact tacagaaag tttatgacat tgtaacaaaa    3600
gttgggaatt ccatccgaag ttgtgatgtt gtggaagtaa tgctttaacc tccttttttc    3660
cttttaattg taaaattatt gtcaattttt tttataacaa atatcctatt tctgggatc     3720 aatatccacc cacaattgat gctaataaaa aaaaaaatta agcttttat tcttgcttac    3780 agggaggaaa gtgtggtatt tatggtgcca attgcccaga atggataatt agcatggagg    3840
tatgatcatt ctggcatgtt tcatctgatt tgcacagtgg acatcccaag ttacttagat    3900
gtcgctataa cttgtttctt tggatcatac tatttgctac caaattgctt gttgcccgaa    3960
atgtttacta atgttgcaag attgatacag gcctgcaacg ctcatggact ctattgtgtt    4020
cctttatatg acactttggg tatttcttct tgagatccaa caaaagcatt ctttcagttt    4080
ttgccaaaca actacctttc tctaacaacc atcttatgtg tattatgtac tcttcatata    4140
gtctgtgatc ataatatcct taaactcttt aaattattct tgcattccaa cgcgcctgct    4200 actcttttg aatgtttgat acgttgctac atatttgtag gtgccggtgc tgtggagttt     4260
atcatatgcc atgcagaaat ttctattgct tttgtagagg aaaagaagat taatgaggta    4320
tgcctgttta catctatatt tgaaacccta gtagtgatat ggcaactact gggaaagata    4380
```

-continued

```
cttctagata cttgcaaaaa taagatatct atctacaaaa tagattcgat gtttttatttt    4440
tattatcagc atttgcttct atgcttgctg ctcacttatg catagttgat attgatacaa    4500
gaatctgtaa tttcacaaat tttctgttct ttttctttt gggtttctca tgtaaggttt    4560
ttcttttcc tttcagctgt tcaaaacatt tccagcctca acagaacact tgaaaagtaa    4620
gctatctgat tatttagggg gattcttgaa atagtacgtt acaaattatt tatgtccatg    4680
tattttgct atgcagcaat tgttagcttc gggaaggtaa cacctgagca aaggcagaa    4740
gctgagaagc atggtttgaa gatatatcct tgggaggaat ttttgcaact ggtaagctct    4800
ttgctctgtt attttccact tcaatttatc agaaataaaa tttattctgc tgaactaatt    4860
gtgtctattt tagcagactg ccatcctgtt agttacgagt tcagatgaag ccatatggct    4920
gtagaaaaca tgcttctggc agtgcttaat atgaactagg cttcattaca tttttcatgca    4980
tgcgcctata tcttttttcc ttagctaacc gttattggat tgatggattt taacctgtag    5040
atgacttatg ttctgattta agctcttatg tctgtttctt gcaggagaa aataagaatt    5100
atggtcttcc ggtgaagaag aaaactgata tctgcacgat aatgtatact agtggaacaa    5160
ctggtgatcc aaagggagta ttgatttcaa atgatatat tgttactctt atagcagggg    5220
tgaaacgcct gctggggagt gtaaatgaac aggtgacctt tcatttat ttttgaccat    5280
ttcaccagtc acttggtttg atctgtcgtt tcttttcttt cctccaccaa atttgacatg    5340
attgttccct tgttttccct ttctcatttg tttgtttctt gtgaaattta cagttgacta    5400
tgaaggatgt atatatttct tatcttcctc ttgctcatat ctttgaccgg gtgattgagg    5460
aattatttat ttcgcatggt gcttcaatag gattttggcg tggggtaagc atgattagtt    5520
agtactctga caacaaatac gggttcattc aaatcagcaa gtgcttattt gtttcatctt    5580
caggatgtga aactattggt cgaagatatt ggagagctaa agccaagtat cttctgtgct    5640
gttcctcgtg tcttagatag aatttattca ggtaaactt cttatattcg tggattaggc    5700
aatgtcattt ttgggttgtt tgtggaggtt atactaagca acctggaaca tgtactagct    5760
ggaaaacttg tcttaattta cttatttta gtatttataa atgaaacaaa actagattga    5820
ttcacttttc tgttaaatac aatgaatata tactcagctt ttttcagaag atgcatgttc    5880
tcagctgtga gattgtcata acctttgtac attatcaggt ttactacaga agatttcttg    5940
cgggcggctt attgaaaaag aagatgtttg atttagcata cacatagtaa gttactctca    6000
tatttcagt ttcttatgtg aagctgttca ttttatctgc tggccgccca aaaatattga    6060
ttggaaatag agttaaattg ctctattagt tctgccactg cagactcacc ggagtaaagg    6120
aaaataaaag atatttgggc attctctaac aagcaacagg gtcaaaagca tattttttcct    6180
tgtagacaaa tatagaattt gttagagttg tgtgacccaa attctagtta aaaaaaagtg    6240
gcaagatagg gggatttgtg ggggcatcgg aggcccccac ggtacggtac agactgcaca    6300
agtggaattc gtataaaagt acacttcttc tatttgatat tgatttgaat aaggtgtttc    6360
aaccttattg cattgcttct attaggtttt gattagaata aggtttatag gtcgtcgtct    6420
ctctctgccc gtggttttgt gtgttatatt tttaccctct ttctttacga ttcattgtca    6480
ttatcgaggt ttgttttttca cagaattgtc tcaatccctt tgggtttatg agcttttgca    6540
ttagtagaga tccatttgca gtctgtgatt gcacttttcg tgaatatgtt taacagagtt    6600
actgaatcag gattacggtt tcttggcttt gattttacta atatctgaca tctgtgataa    6660
cctacagcaa atactacaac atgaagaagg gccgcaaaca tggagaagca tctccaattt    6720
gtgacaaaat tgtatttagt aaggtgatga aagtcttcat tgatacatta tatgcacgag    6780
```

-continued

```
gctccttgaa tattggccaa agcccatta  aatcacattt  acctgcaaca  taatcctctt    6840
gactactcaa atctcatgtt gagttgtaat ttttctcagg taaagcaagg attgggaggg    6900
aatgtgcggc ttattctatc tggtgcagca cctctttcag ctcatgtgga agagttcttg    6960
cgagttgtgg catgttgtca tgttctgcaa ggatatggta tagttgaagt cagcctttgt    7020
gcttgtgata agttcttttt ttcccttac  cagctgtgca cactggctgc aacatgaaca    7080
tttattatta tgttgatcca aatgtaggtc tgacggagag ttgtgcgggg agttttgtct    7140
ctttacctaa tgaattgtca atgcttggta ctgtggggcc tcccagtacc aaacatagat    7200
gtacgcctgg aatctgttcc cgaaatgaat tatgatgccc ttgctagcac accacggggg    7260
gaaatttgta tcaaaggaaa tacattattc tcaggatact acaaacgtga agacctcacc    7320
cgtgaagtat tgattgatgg atggttccac acaggtcttc caacttttgt ttctttaag    7380 gttctatgca ttattagttt ttatctataa gttgaagacc ttgaatcttt gtgcattagg    7440
ggatattgga gagtggcaac ctaatggaag catgaagatt attgatcgaa agaagaacat    7500
ttttaagctt tcacaaggtg aatatgttgc tgttgagaac ctggagaaca tttacggtct    7560
cgtgtcagct attgattcgg tacatctctt atgctctctt tgatacatta acatacactg    7620
cttctcggat atgtagccat gcactgaatg ttggtcaaac gtaaaattga ttttgaaatg    7680
attggcaaat taaacatttt cttcttatg  ttaccttatg attgcattcc ttttttagca    7740
ctaggtttca acccattgcc attgatggtt gcttgattga acaaaaataa acataataat    7800
cgaaatatgc atgtcatgtt acagtgtttt tatcgtatca gttgtgtaaa catgtgtcaa    7860
aatcctttaa cagaaatatg acaaatgtac taaatatgtt aaatcatgct taagcgcatc    7920
atatggtatc taaatttgtc atacatatat gtcatggaag tgatgtaaaa taaactatag    7980
tttatgtcag atttgtaatt tacttgctgg agattggcat tcttttaaac ttttcagttt    8040
catgtcttta tcaatttcag atatggattt acggaaacag ctttgagtcg ttccttgttg    8100
cggttgttaa ccccaataag gaagcacttg aaagctgggg tgccgacaat aacgtaagtg    8160
gtgacttcga gtccctctgt caaaccccca aggccaaaga gttcatactt ggggagctcg    8220
caaagactgg caaagagaaa aaggttagtt attcatgctt tttgcccct  ttttttatttt    8280 tcaaaattta tgaaatatgg gtttatcaat tcatactgaa atattataat ctttactcag    8340
ctaaaaggtt ttgaattctt tggatcc                                        8367
```

<210> SEQ ID NO 2
<211> LENGTH: 2454
<212> TYPE: DNA
<213> ORGANISM: Arabidopsis sp.

<400> SEQUENCE: 2

```
gggaagctta tctacttgaa gttttggtag cccaatgaaa tactctcgta aatctagagt      60
tattagtgta aaccctaaag ggatcaaatt gtataaattt aaatccctta tgactttcaa     120
ttgtagatag actctaatct cgatcatgga tgtaactcaa tctatttgtt gggtttgggg     180
tgattacttc aattcattcc attcatagtt gtgaatatat ttgagagtat ttacgcaaac     240
atttggtgtg tgctattttt cctttggtct tttgttcttc gttgcccatt cgttcgagtt     300
tgctttcgct atatttaat  gccttagaaa attttgcga  gaattctcat tttgtgagag     360
ttaagcgaac ttagaattat tttttttaaa atcgcttaag gctgtatggt ctgtgagact     420
aaaattctag tctcgtaaca ctaatacaat cacaagtaat ttacattgtt caagttctta     480
```

|  |  |  |  |  | |
|---|---|---|---|---|---|
| ttcacataag | cggttggata | aagaaaatta | aaaaaaaaca | atcggatata | attacaaaaa | 540 |
| aataaattga | aatgtgcaat | aatacaaata | ataattattg | ctaaaggtaa | ataaaaaatg | 600 |
| taaataatta | tcaatgaagt | ttgaaacctt | aaatggtgaa | gtttgtgtca | actaatagaa | 660 |
| gaaaaaataa | attatttata | taactctact | aatgtattat | tttattttgt | aaaattgatt | 720 |
| tatttatatt | atttctacta | aattgatgtg | gaattagtga | tatctactta | attaactata | 780 |
| tataattata | atgaatctcc | gggactgtga | ctggtcaaag | atcataaagt | ggtatccaat | 840 |
| aaatttaaaa | tgcacttgta | aaatattaga | ctcatgatgg | cactgaggcg | gaggtgaaga | 900 |
| ggcggcaaag | cacatggaga | agctatatag | aaaattcttt | cacgaaaaag | gcaactcttg | 960 |
| gcttgtgtgt | tgggaattgt | gttaagaact | ggattatata | aaaacaatta | tatggggaaa | 1020 |
| ggaaatggtc | cactgtcaat | agtttactat | aagcaagttg | gagatataaa | attaaatata | 1080 |
| tattcagtac | atatacgagt | ttgagcaaca | aaattagaga | tcttttttgt | caagttgata | 1140 |
| tcttcaattt | tataacgtaa | atgttctttt | gaaggcaaca | gtaatgatat | atatatatgt | 1200 |
| agaagaaatt | taactaaaaa | tagataatta | ggcttaattt | aattaattca | agtgcaattg | 1260 |
| ttttatcata | atatatatta | cattacaagg | cttgaattat | tcatatttta | aatttattta | 1320 |
| ttagttaaca | aagtaattat | tggtgcaaaa | ataaataaat | tattacccca | ttatctattt | 1380 |
| tcttaaataa | aaaatatat | tatatatgcc | atttactctc | tttaaaaaaa | tttaatttac | 1440 |
| aaataaacta | ataaatttgt | atatgatgat | ttcgaatgag | ggttttaata | cagttatcat | 1500 |
| gatgatttca | atacaatggt | tccaaatgaa | taaggattcc | actacaacat | taaactcacc | 1560 |
| ataatggtga | ttccaattga | gtgttcctac | ataattatca | tcataattct | tacttggcag | 1620 |
| gatacaaaaa | ataataatgg | gtaaggtaat | taaaaattaa | aataattatc | aataaagttt | 1680 |
| ttattatggt | gacaaagttt | gataatcatt | attaaattat | taattgagta | aaatatttaa | 1740 |
| atatagtaat | gtatatataa | tgaatctccg | gcgatgttgg | ctgttcaaag | atcataaaat | 1800 |
| ccaatacatt | taaaatgcag | ctgtaaaata | tgatgtgaag | ggcggatacc | acacatggag | 1860 |
| aagccatata | gaaatttctt | ccggtaccat | gaaaaaggcg | actcttagct | tgtgtgttgg | 1920 |
| gaattgtgtt | aagttatatg | ggaaaggaaa | tattccactg | tcaatagttt | attataagca | 1980 |
| agtgggagaa | acaaaattaa | atatgttatt | ttgaaggcaa | cagtaataat | ataattataa | 2040 |
| attaaaataa | cataatttag | gcttaattta | attaatggta | aactataaaa | aaaagtcatt | 2100 |
| tttgtttgct | tcagattaca | ttttagtcac | ttatgtttga | aatgttacgt | tttagtcact | 2160 |
| tacattaccg | ttttgttacg | aagtggtcac | tttaccatta | aactctatta | cctccctaac | 2220 |
| gacagtccta | cgtggcagtc | aaaatgaatt | ttaaatgcta | acttggacgt | ccagttgctg | 2280 |
| ggacattttc | cggttcacct | acagccacct | aatacttagg | cgctatatat | tttcccaaaa | 2340 |
| ttattctcca | catttcactc | ccagagccct | ccatctatgt | agagagctgt | aagagagaat | 2400 |
| ataaaaaagg | gaaagctagc | tgaggatcgt | ttgattttgg | acattttggg | atcc | 2454 |

<210> SEQ ID NO 3
<211> LENGTH: 275
<212> TYPE: DNA
<213> ORGANISM: Arabidopsis sp.

<400> SEQUENCE: 3

|  |  |  |  |  | |
|---|---|---|---|---|---|
| ggtcactgtg | acgtgccgtg | gctactgtga | aacgagccgt | ggctactgtg | aacgtgccgt | 60 |
| ggctactgtg | aacgagccgt | ggctactgtg | aacgtgccgt | ggctactgtg | aacgtgccgt | 120 |

```
ggctactgtg aacgagccgt ggtcactgtg atacgtgccg ggagttttgt ctctttacct      180
aatgaattgt caatgcttgg tactgtgggg ccccatacca aacatagatg tacgcctgga      240
atctgttccg aaaaaaaaaa aactgaattc cgagt                                 275
```

ISOLATION AND CHARACTERISATION OF AN ANTHER-SPECIFIC PROMOTER (COFS) IN COTTON

CROSS REFERENCE TO RELATED APPLICATIONS

This application is a national phase application under 35 U.S.C. § 371 of International Application No. PCT/SG01/00022, filed Jan. 17, 2001, and claims priority therefrom.

BACKGROUND OF THE INVENTION

1. Technical Field

The present invention relates to the field of plant molecular biology. In particular, the invention pertains to cotton promoters and their uses in creating transgenic plants, and more specifically to cotton anther-specific promoters.

2. Description of the Background Art

Cotton is the most extensively used natural fiber in the textile industry. Annual production of cotton worldwide is over 100 million bales valued at 45 billion U.S. dollars. Although significant improvements have been made in quality and yield by means of classical breeding in the past decades, the potential for further improving the properties of cotton through classical breeding is limited due to requirements for species compatibility and available traits. Genetic engineering provides novel approaches for further improving cotton by introducing genes to create new germplasms with highly desirable characteristics, for example, insect pest resistance.

The anther is the male reproductive organ in flowering plants. Anther development can be divided into two general phases. During phase 1, most of specialized cells and tissues differentiate, microspore mother cells undergo meiosis and tetrads of microspores are formed. During phase 2, microspores are released from tetrads followed by pollen grain maturation, tissue degeneration, dehiscence and pollen release. Genes specifically expressed during anther and pollen development have been studied in a few plant species. Allen and Lonsdale, *Plant J.* 3:261–271, 1993; Bird, et al., *Plant Mol. Biol.* 11:651–662, 1988; Brown and Crouch, *Plant Cell* 2:263–274, 1990; Grierson et al., *Nucl. Acids Res.* 14:8595–8603, 1986; Hanson, et al., *Plant Cell* 1:173–179, 1989; Ursin et al., *Plant Cell* 1:727–736, 1989; John and Petersen, *Plant Mol. Biol.* 26(6):1989–1993, 1994; Atanassov et al., *Plant Mol. Biol.* 38:1169–1178 1998; Liu et al., *Plant Mol. Biol.* 33:291–300, 1997; Treacy et al., *Plant Mol. Biol.* 34:603–611, 1997; Agnes et al., *Plant Mol. Biol.* 40:857–872, 1999. Among the 20,000 to 25,000 expressed genes in tobacco anther, only 10,000 genes are anther-specific. Kamalay and Goldberg, *Proc. Natl. Acad. Sci. USA* 81:2801–2805, 1984; Koltunow, et al., *Plant Cell* 2:1201–1224, 1990.

A promoter is a DNA fragment which determines the temporal and spatial specificity of gene expression during plant and animal development. Many tissue-specific genes and their promoters have been identified and isolated from a wide variety of plants and animals over the past decade, including cotton tissue-specific genes and promoters. Loguerico et al., *Mol. Gen. Genet.* 261(4/5):660–671, 1999; Kawai et al., *Plant Cell Physiol.* 39(12):1380–1383, 1998; Song and Allen, *Biochem. Biophys. Acta* 1351(1):305–312, 1997; Ma et al, *Biochim. Biophys. Acta* 1344(2):111–114, 1997; John, *Plant Mol. Biol.* 30(2):297–306, 1996; Rinehart et al., *Plant Physiol.* 112(3):1331–1341, 1996; Hasenfratz et al., *Plant Physiol.* 108(4):1395–1404, 1995; John and Peterson, *Plant Mol. Biol.* 26(6): 1989–1993, 1994; John and Crow, *Proc. Natl. Acad. Sci. USA* 89(13):5769–5773, 1992. These plant tissue-specific promoters can be used to control the expression of foreign genes in transgenic plants in a tissue-specific manner that will dominate the majority of the second generation of transgenic crops. Some plant tissues do not express high levels of the transgene in all desired tissues or the particular desired tissue. In transgenic Bt cotton, for example, Bt gene expression level is extremely low in the flower, including in the anther, resulting in little protection from pest insects in these tissues. To achieve better control of pest insects of cotton, it would be highly advantageous to identify anther-specific promoters which can produce higher levels of gene expression in these tissues.

SUMMARY OF THE INVENTION

Accordingly, the present invention provides a promoter that is cotton another-specific, comprising the promoter of the cotton CoFS gene. The invention also provides a cotton anther-specific promoter comprising SEQ ID NO:2. In yet a further embodiment, the invention provides a transgenic plant expressing a transgene under control of a cotton anther-specific promoter of the cotton CoFS gene.

DETAILED DESCRIPTION OF THE PREFERRED EMBODIMENT

An anther-specific gene (CoFS) and its corresponding promoter were isolated from cotton by differential display assay. The activity and tissue specificity of the isolated promoter was confirmed in transgenic tobacco plants using the CoFS promoter to control the expression of the GUS reporter gene.

Figure 1:
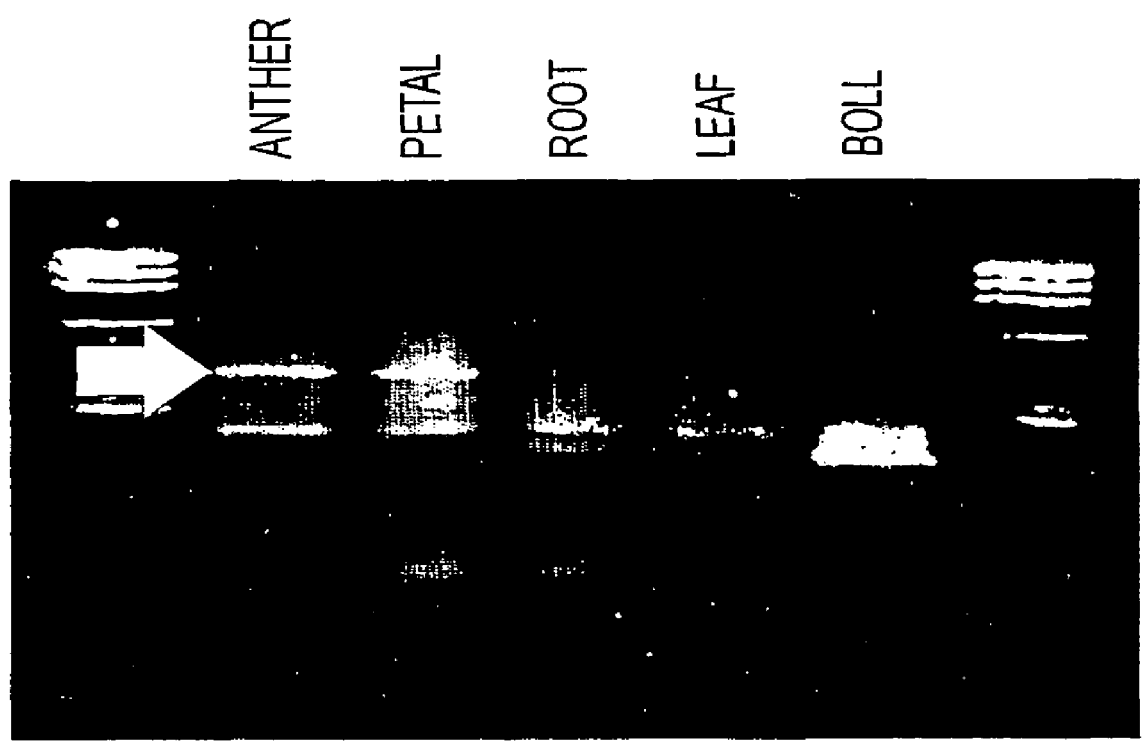
FIG. 1 shows the results of a CoFS cDNA differential display assay.

Northern blot analysis of cDNAs from a variety of cotton tissues showed that a cDNA clone comprising the CoFS gene was strongly expressed in anthers, and also expressed in petal tissue, but less or not at all in other tissues. See FIG. 1.

An anther-specific gene (named CoFS) was isolated from cotton. The isolated complete CoFS cDNA is 8.4 kb in length. See Table I. Based on the CoFS cDNA sequence, a CoFS promoter fragment (2.6 kb) was isolated. See Table II. Comparing the nucleotide and predicted polypeptide sequences of the cotton CoFS gene with published sequences revealed that the gene was about 54–58% identical at the amino acid level with acyl-CoA synthetase (probable long-chain-acid cCoA ligase, EC 6.2.1.3) genes from some plants such as *Brassica napus* (X94624) and Arabidopsis (AL078468, AL161560). Less homology was found at the nucleotide level, indicating that CoFS is a novel gene found in cotton. Analyzing the CoFS gene sequence revealed that it may contain 9–10 exons and 8–9 introns in its open reading frame, based on amino acid sequences of the known acyl-CoA synthetases.

The CoFS promoter fragment was fused with the GUS gene to construct gene expression vectors for analyzing the function of the promoter. Transgenic tobacco plants with the CoFS promoter/GUS fusion genes were identified by Southern blot hybridization. In the transgenic plants studied, GUS activity was detected in anther, and weakly in ovaries, styles and stigmas, but not in petals or other tissues. This result, together with Northern blot analysis, indicates that the CoFS promoter is anther-specific in cotton. The promoter controls specific gene expression at the transcriptional level in cotton anthers. The isolated promoter may be used in improving expression of desired genes in anther and related tissues of the plant sexual organs to create new plant varieties, thereby enhancing quality and yield of the plant by gene manipulation.

The promoters of the present invention are useful in creating transgenic plants, especially including cotton, having improved expression of the transgene in anther tissue. Better expression of protective genes, such as the Bt gene, in anther tissue results in a plant with increased resistance to Bt-sensitive pests. Genes which may be expressed under the control of this promoter include any gene suitable for the purpose.

TABLE I

Sequence of the CoFS Gene From Cotton (SEQ ID NO:1).

CCTCACATTTAAGCGGAAAAAAATATTAACTAATTACTAATTACTAAGGTCATGGGT

TGCGCATTAAAGTTCACTGACGATTGTGCAAATGATGTTCCATAGAGCTTAATTGAT

GAAATGGGAACTCATGACCCGCTTGAAGTAACTCGACTTGTAGAACTCATGAAGAA

GCTTATCTACTTGAAGTTTTGGTAGCCCAATGAAATACTCTCGTAAATCTAGAGTTAT

TAGTGTAAACCCTAAAGGGATCAAATTGTATAAATTTAAATCCCTTATGACTTTCAA

TTGTAGATAGACTCTAATCTCGATCATGGATGTAACTCAATCTATTTGTTGGGTTTGG

GGTGATTACTTCAATTCATTCCATTCATAGTTGTGAATATATTTGAGAGTATTTACGC

AAACATTTGGTGTGTGCTATTTTTCCTTTGGTCTTTTGTTCTTCGTTGCCCATTCGTTC

GAGTTTGCTTTCGCTATATTTTAATGCCTTAGAAAATTTTTGCGAGAATTCTCATTTT

GTGAGAGTTAAGCGAACTTAGAATTATTTTTTTTAAAATCGCTTAAGGCTGTATGGT

CTGTGAGACTAAAATTCTAGTCTCGTAACACTAATACAATCACAAGTAATTTACATT

GTTCAAGTTCTTATTCACATAAGCGGTTGGATAAAGAAAATTAAAAAAAAACAATC

GGATATAATTACAAAAAAATAAATTGAAATGTGCAATAATACAAATAATAATTATT

GCTAAAGGTAAATAAAAAATGTAAATAATATCAATGAAGTTTGAAACCTTAAATG

GTGAAGTTTGTGTCAACTAATAGAAGAAAAAATAAATTATTTATATAACTCTACTAA

TGTATTATTTTATTTTGTAAAATTGATTTATTTATATTATTTCTACTAAATTGATGTGG

AATTAGTGATATCTACTTAATTAACTATATATAATTATAATGAATCTCCGGGACTGT

GACTGGTCAAAGATCATAAAGTGGTATCCAATAAATTTAAAATGCACTTGTAAAATA

TTAGACTCATGATGGCACTGAGGCGGAGGTGAAGAGGCGGCAAAGCACATGGAGA

AGCTATATAGAAAATTCTTTCACGAAAAAGGCAACTCTTGGCTTGTGTGTTGGGAAT

TGTGTTAAGAACTGGATTATATAAAAACAATTATATGGGGAAAGGAAATGGTCCAC

TGTCAATAGTTTACTATAAGCAAGTTGGAGATATAAAATTAAATATATATTCAGTAC

ATATACGAGTTTGAGCAACAAAATTAGAGATCTTTTTTGTCAAGTTGATATCTTCAA

TTTTATAACGTAAATGTTCTTTTGAAGGCAACAGTAATGATATATATATATGTAGAA

GAAATTTAACTAAAAATAGATAATTAGGCTTAATTTAATTAATTCAAGTGCAATTGT

TTTATCATAATATATATTACATTACAAGGCTTGAATTATTCATATTTTAAATTTATTT

ATTAGTTAACAAAGTAATTATTGGTGCAAAAATAAATAAATTATTACCCCATTATCT

ATTTTCTTAAATAAAAAAATATATTATATATGCCATTTACTCTCTTTAAAAAAATTTA

ATTTACAAATAAACTAATAAATTTGTATATGATGATTTCGAATGAGGGTTTTAATAC

AGTTATCATGATGATTTCAATACAATGGTTCCAAATGAATAAGGATTCCACTACAAC

TABLE I-continued

Sequence of the CoFS Gene From Cotton (SEQ ID NO:1).

ATTAAACTCACCATAATGGTGATTCCAATTGAGTGTTCCTACATAATTATCATCATA

ATTCTTACTTGGCAGGATACAAAAAATAATAATGGGTAAGGTAATTAAAAATTAAA

ATAATTATCAATAAAGTTTTTATTATGGTGACAAAGTTTGATAATCATTATTAAATTA

TTAATTGAGTAAAATATTTAAATATAGTAATGTATATATAATGAATCTCCGGCGATG

TTGGCTGTTCAAAGATCATAAAATCCAATACATTTAAAATGCAGCTGTAAAATATGA

TGTAAAGGGCGGATAAAGCACATGGAGAAGCCATATAGAAATTTCTTCCATGAAAA

AGGCGACTCTTAGCTTGTGTGTTGGGAATTGTGTTAAGTTATATGGGAAAGGAAATA

TTCCACTGTCAATAGTTTATTATAAGCAAGTGGGAGAAACAAAATTAAATATGTTAT

TTTGAAGGCAACAGTAATAATATAATTATAAATTAAAATAACATAATTTAGGCTTAA

TTTAATTAATGGTAAACTATAAAAAAAAGTCATTTTTGTTTGCTTCAGATTACATTTT

AGTCACTTATGTTTGAAATGTTACGTTTTAGTCACTTACATTACCGTTTTGTTACGAA

GTGGTCACTTTACCATTAAACTCTATTACCTCCCTAACGACAGTCCTACGTGGCAGT

CAAAATGAATTTTAAATGCTAACTTGGACGTCCAGTTGCTGGGACATTTTCCGGTTC

ACCTACAGCCACCTAATACTTAGGCGCTATATATTTTCCCAAAATTATTCTCCACATT

TCACTCCCAGAGCCCTCCATCTATGTAGAGAGCTGTAAGAGAGAATATAAAAAAGG

GAAAGCTAGCTGAGGATCGTTTGATTTTGGACATTTTGATGAAACGGCCTGGAAATA

ATTTTGTAATAGAGGTAGAGAAAGGTAAAGACCCCAGCGATGGACAGCCGTCGATC

GGTCCTGTTTATCGCAGTTCTTTTGCTGCTAATGGATTCCCTGCTCCGATTCCTGGAA

TGGAGAGTTGCTGGGACATTTTCCGGTTCGTTTTTAGCTTTCTCTTTTTTACTTTACGC

TTCTTGCTTGGCTGCTAAGAAAATAAGGATACTAGGAGAAGATTTGACTTCTTCTAT

TCTTTGCTTTGATTTCAGATGGCTTTCGCAATAGTTGCCATTTTTTTTGAATTTTTACT

TCCCCTTTTTTAAGTTGAGTAGATTTTTCTTCTAATTTGTTGGCTTTGTTATTTTTTAT

TTCGCGACGAGGTGGCGATGAAATCGAGAAACGTACTTTTAAGGATCCTATGAGAA

AGTTATATGCAAGATCGAAACGCCTAATATTTGAAACTATTGAATTTTAACGCTCAC

ACAGAGCAAGAATCGAGTTACTGGTATTTCCATTCTTATAGCTGAAAGATTGATGGC

TTTCATTCAACTCAATGTAAAACTGTGAAATAAATTGTTTAATAGTAGTAATTATTTT

GGTTTTGATGCTTATGTGATGTGGAGATTAAAATATTGCCTCCTTATAACTTAGCTGA

ACCGTAGATATGGGCTGATTGAACTTGCTAACTAACTGTATGACAGCTCCTATTTAC

GAAAAAGTAATATTTTATTTGAGGATGATGATTTCGATTTCATTTTCTCCTTGCAGTA

TGTCAGTTGAGAAATATCCTGACAACCATATGCTTGGTCGCCGACAGATTGTGGATG

GGAAAGTATGTTGCTGCTGCAGTTTCCTTTTTTCTTGTTACTTTTGCGTTCTGTTTGTA

GTGCGGCCTTTGACTTTTAGTTCATGTATCTAAATTGACATGCTTTGATTGCAGGCTG

GAAAATACGTGTGGCAAACTTACAGAGAAGTTTATGACATTGTAACAAAAGTTGGG

AATTCCATCCGAAGTTGTGATGTTGTGGAAGTAATGCTTTAACCTCCTTTTTTCCTTT

TAATTGTAAAATTATTGTCAATTTTTTTTATAACAAATATCCTATTTCTGGGGATCAA

TATCCACCCACAATTGATGCTAATAAAAAAAAAAAATTAAGCTTTTTATTCTTGCTTA

CAGGGAGGAAAGTGTGGTATTTATGGTGCCAATTGCCCAGAATGGATAATTAGCAT

GGAGGTATGATCATTCTGGCATGTTTCATCTGATTTGCACAGTGGACATCCCAAGTT

ACTTAGATGTCGCTATAACTTGTTTCTTTGGATCATACTATTTGCTACCAAATTGCTT

TABLE I-continued

Sequence of the CoFS Gene From Cotton (SEQ ID NO:1).

GTTGCCCGAAATGTTTACTAATGTTGCAAGATTGATACAGGCCTGCAACGCTCATGG

ACTCTATTGTGTTCCTTTATATGACACTTTGGGTATTTCTTCTTGAGATCCAACAAAA

GCATTCTTTCAGTTTTTGCCAAACAACTACCTTTCTCTAACAACCATCTTATGTGTAT

TATGTACTCTTCATATAGTCTGTGATCATAATATCCTTAAACTCTTTAAATTATTCTT

GCATTCCAACGCGCCTGCTACTCTTTTTGAATGTTTGATACGTTGCTACATATTTGTA

GGTGCCGGTGCTGTGGAGTTTATCATATGCCATGCAGAAATTTCTATTGCTTTTGTAG

AGGAAAAGAAGATTAATGAGGTATGCCTGTTTACATCTATATTTGAAACCCTAGTAG

TGATATGGCAACTACTGGGAAAGATACTTCTAGATACTTGCAAAAATAAGATATCTA

TCTACAAAATAGATTCGATGTTTTATTTTATTATCAGCATTTGCTTCTATGCTTGCTG

CTCACTTATGCATAGTTGATATTGATACAAGAATCTGTAATTTCACAAATTTTCTGTT

CTTTTTTCTTTTGGGTTTCTCATGTAAGGTTTTTCTTTTCCTTTCAGCTGTTCAAAAC

ATTTCCAGCCTCAACAGAACACTTGAAAAGTAAGCTATCTGATTATTTAGGGGGATT

CTTGAAATAGTACGTTACAAATTATTTATGTCCATGTATTTTTGCTATGCAGCAATTG

TTAGCTTCGGGAAGGTAACACCTGAGCAGAAGGCAGAAGCTGAGAAGCATGGTTTG

AAGATATATCCTTGGGAGGAATTTTTGCAACTGGTAAGCTCTTTGCTCTGTTATTTTC

CACTTCAATTTATCAGAAATAAAATTTATTCTGCTGAACTAATTGTGTCTATTTTAGC

AGACTGCCATCCTGTTAGTTACGAGTTCAGATGAAGCCATATGGCTGTAGAAAACAT

GCTTCTGGCAGTGCTTAATATGAACTAGGCTTCATTACATTTTCATGCATGCGCCTAT

ATCTTTTTTCCTTAGCTAACCGTTATTGGATTGATGGATTTTAACCTGTAGATGACTT

ATGTTCTGATTTAAGCTCTTATGTCTGTTTCTTGCAGGGAGAAAATAAGAATTATGGT

CTTCCGGTGAAGAAGAAAACTGATATCTGCACGATAATGTATACTAGTGGAACAAC

TGGTGATCCAAAGGGAGTATTGATTTCAAATGATAGTATTGTTACTCTTATAGCAGG

GGTGAAACGCCTGCTGGGGAGTGTAAATGAACAGGTGACCTTTTCATTTTATTTTTG

ACCATTTCACCAGTCACTTGGTTTGATCTGTCGTTTCTTTTCTTTCCTCCACCAAATTT

GACATGATTGTTCCCTTGTTTTCCCTTTCTCATTTGTTTGTTTCTTGTGAAATTTACAG

TTGACTATGAAGGATGTATATATTTCTTATCTTCCTCTTGCTCATATCTTTGACCGGG

TGATTGAGGAATTATTTATTTCGCATGGTGCTTCAATAGGATTTTGGCGTGGGGTAA

GCATGATTAGTTAGTACTCTGACAACAAATACGGGTTCATTCAAATCAGCAAGTGCT

TATTTGTTTCATCTTCAGGATGTGAAACTATTGGTCGAAGATATTGGAGAGCTAAAG

CCAAGTATCTTCTGTGCTGTTCCTCGTGTCTTAGATAGAATTTATTCAGGTAAACTTT

CTTATATTCGTGGATTAGGCAATGTCATTTTTGGGTTGTTTGTGGAGGTTATACTAAG

CAACCTGGAACATGTACTAGCTGGAAAACTTGTCTTAATTTACTTATTTTTAGTATTT

ATAAATGAAACAAAACTAGATTGATTCACTTTTCTGTTAAATACAATGAATATATAC

TCAGCTTTTTTCAGAAGATGCATGTTCTCAGCTGTGAGATTGTCATAACCTTTGTACA

TTATCAGGTTTACTACAGAAGATTTCTTGCGGGCGGCTTATTGAAAAAGAAGATGTT

TGATTTAGCATACACATAGTAAGTTACTCTCATATTTTCAGTTTCTTATGTGAAGCTG

TTCATTTTATCTGCTGGCCGCCCAAAAATATTGATTGGAAATAGAGTTAAATTGCTCT

ATTAGTTCTGCCACTGCAGACTCACCGGAGTAAAGGAAAATAAAAGATATTTGGGC

TABLE I-continued

Sequence of the CoFS Gene From Cotton (SEQ ID NO:1).

ATTCTCTAACAAGCAACAGGGTCAAAAGCATATTTTTCCTTGTAGACAAATATAGAA

TTTGTTAGAGTTGTGTGACCCAAATTCTAGTTAAAAAAAAGTGGCAAGATAGGGGG

ATTTGTGGGGGCATCGGAGGCCCCCACGGTACGGTACAGACTGCACAAGTGGAATT

CGTATAAAAGTACACTTCTTCTATTTGATATTGATTTGAATAAGGTGTTTCAACCTTA

TTGCATTGCTTCTATTAGGTTTTGATTAGAATAAGGTTTATAGGTCGTCGTCTCTCTC

TGCCCGTGGTTTTGTGTGTTATATTTTTACCCTCTTTCTTTACGATTCATTGTCATTAT

CGAGGTTTGTTTTTCACAGAATTGTCTCAATCCCTTTGGGTTTATGAGCTTTTGCATT

AGTAGAGATCCATTTGCAGTCTGTGATTGCACTTTTCGTGAATATGTTTAACAGAGTT

ACTGAATCAGGATTACGGTTTCTTGGCTTTGATTTTACTAATATCTGACATCTGTGAT

AACCTACAGCAAATACTACAACATGAAGAAGGGCCGCAAACATGGAGAAGCATCTC

CAATTTGTGACAAAATTGTATTTAGTAAGGTGATGAAAGTCTTCATTGATACATTAT

ATGCACGAGGCTCCTTGAATATTGGCCAAAAGCCCATTAAATCACATTTACCTGCAA

CATAATCCTCTTGACTACTCAAATCTCATGTTGAGTTGTAATTTTTCTCAGGTAAAGC

AAGGATTGGGAGGGAATGTGCGGCTTATTCTATCGGTGCAGCACCTCTTTCAGCTC

ATGTGGAAGAGTTCTTGCGAGTTGTGGCATGTTGTCATGTTCTGCAAGGATATGGTA

TAGTTGAAGTCAGCCTTTGTGCTTGTGATAAGTTCTTTTTTTCCCTTTACCAGCTGTG

CACACTGGCTGCAACATGAACATTTATTATTATGTTGATCCAAATGTAGGTCTGACG

GAGAGTTGTGCGGGGAGTTTTGTCTCTTTACCTAATGAATTGTCAATGCTTGGTACTG

TGGGGCCTCCCAGTACCAAACATAGATGTACGCCTGGAATCTGTTCCCGAAATGAAT

TATGATGCCCTTGCTAGCACACCACGGGGGAAATTTGTATCAAAGGAAATACATTA

TTCTCAGGATACTACAAACGTGAAGACCTCACCCGTGAAGTATTGATTGATGGATGG

TTCCACACAGGTCTTCCAACTTTTGTTTCTTTTAAGGTTCTATGCATTATTAGTTTTTA

TCTATAAGTTGAAGACCTTGAATCTTTGTGCATTAGGGGATATTGGAGAGTGGCAAC

CTAATGGAAGCATGAAGATTATTGATCGAAAGAAGAACATTTTTAAGCTTTCACAAG

GTGAATATGTTGCTGTTGAGAACCTGGAGAACATTTACGGTCTCGTGTCAGCTATTG

ATTCGGTACATCTCTTATGCTCTCTTTGATACATTAACATACACTGCTTCTCGGATAT

GTAGCCATGCACTGAATGTTGGTCAAACGTAAAATTGATTTTGAAATGATTGGCAAA

TTAAACATTTTCTTTCTTATGTTACCTTATGATTGCATTCCTTTTTTAGCACTAGGTTT

CAACCCATTGCCATTGATGGTTGCTTGATTGAACAAAAATAAACATAATAATCGAAA

TATGCATGTCATGTTACAGTGTTTTTATCGTATCAGTTGTGTAAACATGTGTCAAAAT

CCTTTAACAGAAATATGACAAATGTACTAAATATGTTAAATCATGCTTAAGCGCATC

ATATGGTATCTAAATTTGTCATACATATATGTCATGGAAGTGATGTAAAATAAACTA

TAGTTTATGTCAGATTTGTAATTTACTTGCTGGAGATTGGCATTCTTTTAAACTTTTC

AGTTTCATGTCTTTATCAATTTCAGATATGGATTTACGGAAACAGCTTTGAGTCGTTC

CTTGTTGCGGTTGTTAACCCCAATAAGGAAGCACTTGAAAGCTGGGGTGCCGACAAT

AACGTAAGTGGTGACTTCGAGTCCCTCTGTCAAAACCCCAAGGCCAAAGAGTTCATA

TABLE I-continued

Sequence of the CoFS Gene From Cotton (SEQ ID NO:1).

CTTGGGGAGCTCGCAAAGACTGGCAAAGAGAAAAAGGTTAGTTATTCATGCTTTTTG

CCCCCTTTTTTATTTTTCAAAATTTATGAAATATGGGTTTATCAATTCATACTGAAAT

ATTATAATCTTTACTCAGCTAAAAGGTTTTGAATTCTTTGGATCC

TABLE II

Sequence of the Cotton CoFS Promoter (SEQ ID NO:2).

GGGAAGCTTATCTACTTGAAGTTTTGGTAGCCCAATGAAATACTCTCGTAAATCTAG

AGTTATTAGTGTAAACCCTAAAGGGATCAAATTGTATAAATTTAAATCCCTTATGAC

TTTCAATTGTAGATAGACTCTAATCTCGATCATGGATGTAACTCAATCTATTTGTTGG

GTTTGGGGTGATTACTTCAATTCATTCCATTCATAGTTGTGAATATATTTGAGAGTAT

TTACGCAAACATTTGGTGTGTGCTATTTTTCCTTTGGTCTTTTGTTCTTCGTTGCCCAT

TCGTTCGAGTTTGCTTTCGCTATATTTTAATGCCTTAGAAAATTTTTGCGAGAATTCT

CATTTTGTGAGAGTTAAGCGAACTTAGAATTATTTTTTTTAAAATCGCTTAAGGCTGT

ATGGTCTGTGAGACTAAAATTCTAGTCTCGTAACACTAATACAATCACAAGTAATTT

ACATTGTTCAAGTTCTTATTCACATAAGCGGTTGGATAAAGAAAATTAAAAAAAAAC

AATCGGATATAATTACAAAAAAATAAATTGAAATGTGCAATAATACAAATAATAAT

TATTGCTAAAGGTAAATAAAAAATGTAAATAATTATCAATGAAGTTTGAAACCTTAA

ATGGTGAAGTTTGTGTCAACTAATAGAAGAAAAAATAAATTATTTATATAACTCTAC

TAATGTATTATTTTATTTTGTAAAATTGATTTATTTATATTATTTCTACTAAATTGATG

TGGAATTAGTGTATATCTACTTAATTAACTATATATAATTATAATGAATCTCCGGGAC

TGTGACTGGTCAAAGATCATAAAGTGGTATCCAATAAATTTAAAATGCACTTGTAAA

ATATTAGACTCATGATGGCACTGAGGCGGAGGTGAAGAGGCGGCAAAGCACATGGA

GAAGCTATATAGAAAATTCTTTCACGAAAAAGGCAACTCTTGGCTTGTGTGTTGGGA

ATTGTGTTAAGAACTGGKATTATATAAAAACAATTATATGGGGAAAGGAAATGGTCC

ACTGTCAATAGTTTACTATAAGCAAGTTGGAGATATAAAATTAAATATATATTCAGT

ACATATACGAGTTTGAGCAACAAAATTAGAGATCTTTTTTGTCAAGTTGATATCTTC

AATTTTATAACGTAAATGTTCTTTTGAAGGCAACAGTAATGATATATATATATGTAG

AAGAAATTTAACTAAAAATAGATAATTAGGCTTAATTTAATTAATTCAAGTGCAATT

GTTTTATCATAATATATATTACATTACAAGGCTTGAATTATTCATATTTTAAATTTAT

TTATTAGTTAACAAAGTAATTATTGGTGCAAAAATAAATAAATTATTACCCCATTAT

CTATTTTCTTAAATAAAAAAATATATTATATATGCCATTTACTCTCTTTAAAAAAATT

TAATTTACAAATAAACTAATAAATTTGTATATGATGATTTCGAATGAGGGTTTTAAT

ACAGTTATCATGATGATTTCAATACAATGGTTCCAAATGAATAAGGATTCCACTACA

ACATTAAACTCACCATAATGGTGATTCCAATTGAGTGTTCCTACATAATTATCATCAT

AATTCTTACTTGGCAGGATACAAAAAATAATAATGGGTAAGGTAATTAAAAATTAA

AATAATTATCAATAAAGTTTTTATTATGGTGACAAAGTTTGATAATCATTATTAAATT

ATTAATTGAGTAAAATATTTAAATATAGTAATGTATATATAATGAATCTCCGGCGAT

GTTGGCTGTTCAAAGATCATAAAAATCCAATACATTTAAAATGCAGCTGTAAAATATG

TABLE II-continued

Sequence of the Cotton CoFS Promoter (SEQ ID NO:2).

ATGTGAAGGGCGGATACCACACATGGAGAAGCCATATAGAAATTTCTTCCGGTACC

ATGAAAAAGGCGACTCTTAGCTTGTGTGTTGGGAATTGTGTTAAGTTATATGGGAAA

GGAAATATTCCACTGTCAATAGTTTATTATAAGCAAGTGGGAGAAACAAAATTAAAT

ATGTTATTTTGAAGGCAACAGTAATAATATAATTATAAATTAAAATAACATAATTTA

GGCTTAATTTAATTAATGGTAAACTATAAAAAAAAGTCATTTTTGTTTGCTTCAGATT

ACATTTTAGTCACTTATGTTTGAAATGTTACGTTTTAGTCACTTACATTACCGTTTTGT

TACGAAGTGGTCACTTTACCATTAAACTCTATTACCTCCCTAACGACAGTCCTACGT

GGCAGTCAAAATGAATTTTAAATGCTAACTTGGACGTCCAGTTGCTGGGACATTTTC

CGGTTCACCTACAGCCACCTAATACTTAGGCGCTATATATTTTCCCAAAATTATTCTC

CACATTTCACTCCCAGAGCCCTCCATCTATGTAGAGAGCTGTAAGAGAGAATATAAA

AAAGGGAAAGCTAGCTGAGGATCGTTTGATTTTGGACATTTTGGGATCC

TABLE III

Sequence of a CoFS 275 bp cDNA Fragment (SEQ ID NO:3).

GGTCACTGTGACGTGCCGTGGCTACTGTGAAACGAGCCGTGGCTACTGTGAACGTGC

CGTGGCTACTGTGAACGAGCCGTGGCTACTGTGAACGTGCCGTGGCTACTGTGAACG

TGCCGTGGCTACTGTGAACGAGCCGTGGTCACTGTGATACGTGCCGGGAGTTTTGTC

TCTTTACCTAATGAATTGTCAATGCTTGGTACTGTGGGGCCCCATACCAAACATAGA

TGTACGCCTGGAATCTGTTCCGAAAAAAAAAAAACTGAATTCCGAGT

The following non-limiting examples are included to illustrate the invention.

EXAMPLE 1

Isolation of an Anther-specific cDNA Fragment Encoding a CoFS Sequence Expressed in Cotton Anthers Cotton seeds were surface-sterilised with 70% ethanol for 30–60 seconds and 10% $H_2O_2$ for 30–60 minutes, followed by washing with sterile water. The seeds were germinated on ½ MS medium at 28 C with 16 hr lighting. Cotyledons and hypocotyls were cut from sterile seedlings as transformation explant material. Cotton plants were grown in pots for DNA and RNA extraction. Total RNA was extracted from young fibres, ovaries, anthers, petals, sepals, leaves and roots of cotton using the guanidinium thiocyanate method or SV Total RNA Isolation System (Promega). Poly $(A)^+$RNA was purified using oligo(dT)-cellulose spin columns from an mRNA purification kit (Pharmacia Biotech). Total RNAs from different tissues of cotton were used to reverse-transcribe first-strand cDNAs. These cDNAs were used as templates in differential display PCR.

Differential display analysis was carried out with the Differential Display Kit (Clontech). First-strand cDNA was synthesised with 2 μg total RNA as starting materials of reverse transcription and oligo(dT) as primers at 42 C for 1 hour. Reactions of differential display PCR were carried out with an initial cycle consisting of 94 C for 5 minutes, 40 C for 5 minutes and 68 C for 5 minutes, followed by two cycles consisting of 94 C for 2 minutes and 40 C for 5 minutes and 68 C for 5 minutes, and then 25 cycles consisting of 94 C for 1 minute, 60 C for 1 minute and 68 C for 2 minutes, and a final extension at 68 C for 7 minutes. Target differential display bands were excised and re-amplified for further analysis. PCR fragments, DNA and cDNA fragments were sub cloned into vectors, and plasmid DNA and phagemid DNA prepared with a Qiagen Plasmid Kit were used as templates in PCR reactions. The PCR products were sequenced by autosequencer.

Cotton cDNA was synthesised using a cDNA synthesis kit (Stratagene). Cotton cDNA libraries were constructed by inserting the cDNA fragments into the ZAP express vector (Stratagene). Reproducible anther- and petal-specific differential display products (see FIG. 1) were targeted for further analysis. The cDNAs in each target band were harvested and regenerated by PCR amplification. The isolated cDNAs were subsequently sub cloned into a vector and sequenced.

To confirm which cDNA transcripts specifically accumulated in cotton anthers, cDNA expression patterns were analyzed by Northern blot hybridization with total RNA isolated from cotton fibers, ovules, anthers, petals, sepals, stems, leaves and roots, using probes from the cDNA clones. For Northern blot analysis, RNA samples from different cotton tissues were separated on agarose-formaldehyde gels, and transferred onto Hybond-N nylon membranes by capillary blotting. RNA Northern blots were hybridised in ExpressHyb solution (Clontech) at 68 C with $^{32}$P-cDNA probes prepared by random labelling (Prime-a-Gene Labelling System, Promega). After hybridisation, the blots were washed at 68 C in 0.1×SSC, 0.5% SDS for 30–60 minutes.

Figure 2:
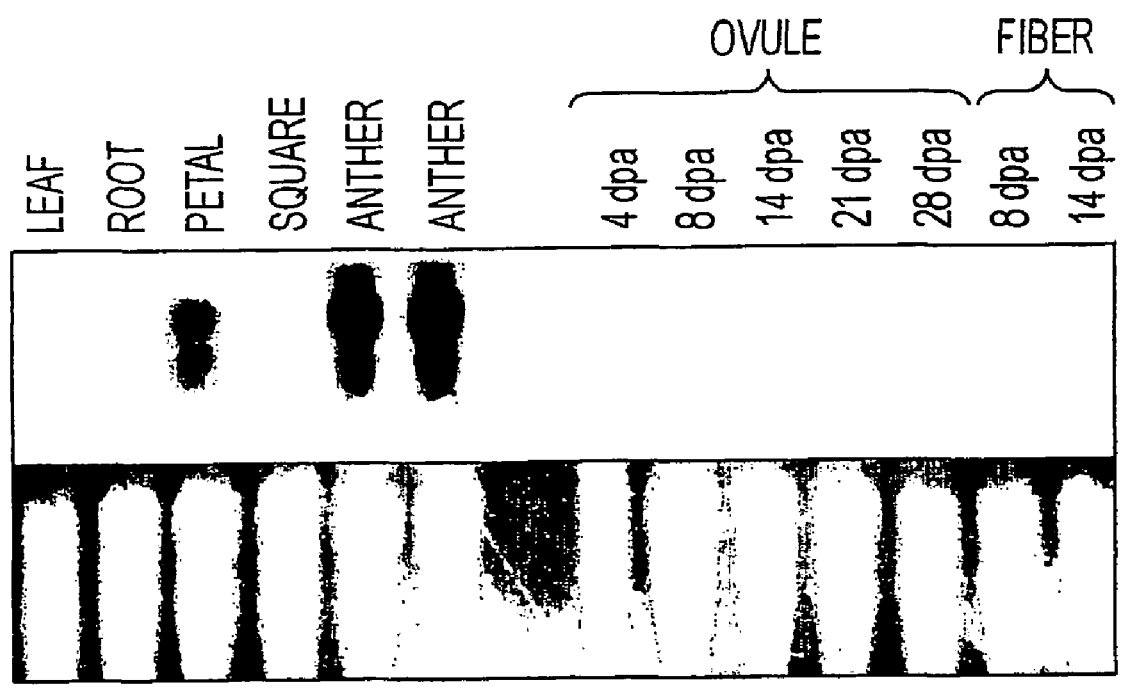
FIG. 2 provides a Northern blot showing CoFS gene expression.

One clone was identified as a 275 bp CoFS cDNA fragment (see Table III). The cDNA fragment was found to share 73% homology with the acyl-CoA synthetase gene (X94624) of *Brassica napus* in a region of 33 amino acids of the open reading frame. Northern blot hybridization revealed the CoFS cDNA transcripts accumulated largely in cotton anthers, and also accumulated more or less in petals, but these transcripts were not detected in RNA from fibers, ovules, stems, leaves and roots (see FIG. 2). This result shows that CoFS cDNA expression is anther-specific in cotton.

EXAMPLE 2

Isolation and Structure Analysis of CoFS Gene

Plant materials from cotton were prepared as in Example 1. Tobacco seeds were surface-sterilized with 70% ethanol for 30–60 seconds and 0.1% $HgCl_2$ for 15 minutes, followed by washing with sterile water. The seeds were germinated on ½ MS medium in light at 28 C, and leaves cut from sterile seedlings were used as experimental materials.

Total DNA was extracted and purified from leaves of cotton and tobacco plants according to the following method. Leaf tissues (z-4 g) were thoroughly homogenised in liquid $N_2$. The homogenized tissues were placed in a 50 ml tube with 20 ml ice-cold extraction buffer and sedimented at 2500 rpm for 15 minutes. After removing the supernatant, each pellet was resuspended in 10 ml lysis buffer and incubated at 65 C for 30 minutes. Ten milliliters chloroform was added to each tube and mixed with the samples. The samples then were sedimented at 3500 rpm for 10 minutes. The supernatant was transferred to a clean tube, and chloroform extraction was repeated once more. The supernatant was transferred to a clean tube, and 0.6 volume isopropanol was added to each tube for DNA precipitation. After centrifuging at 3500 rpm for 30 minutes, the DNA was washed with 70% ethanol. The isolated genomic DNA was then dissolved in sterile water for use.

Cotton genomic DNA libraries were constructed from leaves of cotton plants. DNA was partially digested with BamH I, and the DNA fragments were cloned in the BamH I site of ZAP express vector (Stratagene). The cotton genomic DNA libraries were screened using CoFS gene fragments isolated by Genome Walk PCR as probes.

Genome Walker libraries were constructed using the Universal Genome Walker Kit (Clontech). Genomic DNA from leaves of cotton plants was digested with five restriction enzymes respectively, purified by phenol/chloroform extraction and precipitated in ethanol. The digested DNA was ligated to Genome Walker adaptors.

Two Genome Walker polymerase chain reactions were carried out successively: 1 μl of each Genome Walker DNA library was used as the templates in the primary PCR, and the primary PCR products were used as templates in the secondary PCR. The PCR was started at 95 C for 1 minute, followed by 35 cycles of 95 C for 15 seconds and 68 C for 4 minutes and a final extension at 68 C for 6 minutes. Target PCR bands were purified using a Geneclean Kit (Bio 101).

The screens revealed two CoFS gene positive clones. One clone contained a 4.801 kb cotton CoFS gene region, and the other contained a 3.913 kb cotton DNA fragment covering part of CoFS promoter region. Three CoFS promoter fragments (0.7, 1.4 and 2.6 kb, respectively) were isolated from the cotton Genome Walker libraries. The complete CoFS gene isolated from cotton was 8.4 kb in length, including a 2.6 kb promoter region. The sequences are provided in Tables I and II.

EXAMPLE 3

Functional Analysis of CoFS Promoters

Figure 3:
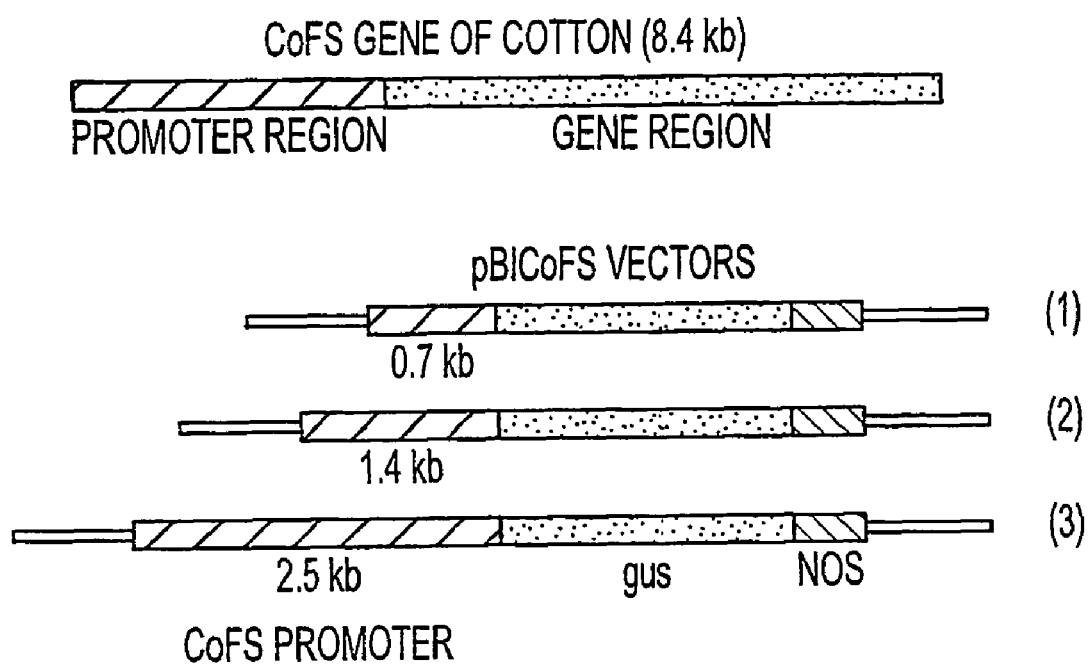
FIG. 3 is a schematic diagram of constructs of CoFS promoter vector constructs and the cotton CoFS gene.

To characterize the function of the CoFS promoter in anther-specific expression of the CoFS gene, a 0.7 kb fragment, a 1.4 kb fragment and a 2.5 kb fragment of the CoFS promoter were fused with the GUS coding sequence in the gene expression vector pBI121 (replacing the CaMV35S promoter), respectively. See FIG. 3.

Vectors were constructed as follows. A Hind III site and a BamH I site were created by PCR at the 5'-end and 3'-end of the 0.7, 1.4 and 2.4 kb CoFS promoter fragments respectively. The Hind III/BamH I fragment was initially sub cloned into pGEM-T vector (Promega). Plasmid DNA containing the CoFS promoter fragments was digested with Hind III and BamH I, and the digested fragment was isolated by agarose gel electrophoresis. Three chimeric CoFS promoter/GUS constructs were generated by insertion of the 0.7, 1.4 or 2.4 kb fragment, respectively, replacing the CaMV 35S promoter, into the Hind III/BamH I sites of pBI121 vector.

The CoFS promoter/GUS fusion gene constructs were used to transform tobacco by *Agrobacterium*-mediated gene transfer, using the pBI121 vector containing a CaMV35S promoter/GUS fusion protein as a positive control. The CaMV35S promoter is a constitutive promoter, active in all plant tissues. Odell et al., *Nature* 313:810–812, 1985; Ow et al., *Proc. Natl. Acad. Sci. USA* 84:4870–4874, 1987; McCabe and Martinell, *Biotechnol.* 11:596–598, 1993.

The binary vectors containing CoFS promoter/GUS fusion genes were transferred into *Agrobacterium tumefaciens* strain LBA 4404. Tobacco transformations were carried out using the leaf-disc method (Horsch, et al., 1985). Tobacco leaves were cut into pieces about 2×2 cm, and immersed in the Agrobacteria suspension for five minutes. The infected tobacco explants were cultivated on MS medium with 1 mg/L 6-BA for 48 hours at 28 C and transferred onto selection MS medium containing 100 mg/L kanamycin and 1 mg/L 6-BA for 20–30 days. Kanamycin-resistant (transformed) shoots were selected. The transformed shoots were cut from the calli and rooted on MS medium with 50–100 mg/L kanamycin. The transformed tobacco plants were transplanted to soil for growing to maturity.

Figure 4A:
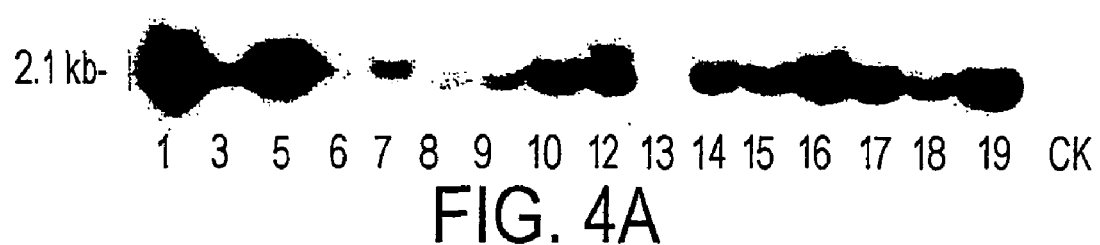
FIG. 4 provides the results of an assay of the expression of the GUS gene under the control of the CoFS gene promoter in transgenic tobacco plants.
Figure 4B:
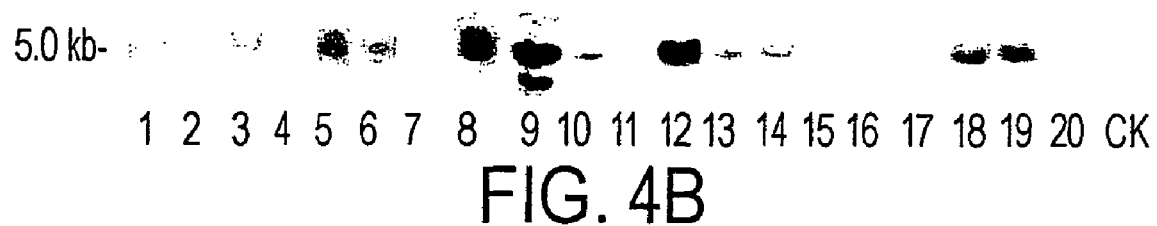

Transgenic tobacco plants possessing the chimeric CoFS promoter/GUS gene (or 35S/GUS gene), and negative control, non-transformed plants were analyzed by DNA Southern blot hybridization and by GUS histochemical assay. For Southern blot analysis, total genomic DNA from the transgenic tobacco leaves was digested with restriction enzymes, separated on agarose gels, and transferred onto Hybond-N nylon membranes by capillary blotting. DNA Southern blots were hybridized in ExpressHyb solution (Clontech) at 68 C with $^{32}$P-DNA probes prepared by random labelling (Promega Prime-a-Gene Labelling System). After hybridization, the blots were washed at 68 C in 0.1×SSC, 0.5% SDS for 30–60 minutes. The $^{32}$P-labelled nylon membranes were exposed to X-ray film at −70 C for autoradiograph. See FIG. 4 for the results.

Figure 5A:
FIG. 5 shows the results of an expression assay of the GUS gene under the control of the CoFS promoter in transgenic tobacco plants.
Figure 5B:
Figure 5C:

Histochemical assays for GUS activity in transgenic tobacco plants were conducted according to a protocol described previously, Jefferson, *Plant Mol. Biol. Rep.* 5:387–405, 1987, with some modifications. Fresh tissues from the plants were incubated in X-gluc (5-bromo-4-chloro-3-indolylglucuronide) solution consisting of 0.1 M sodium phosphate (pH 7.0), 10 mM ethylene diaminetetraacetic acid (EDTA), 0.5 mM potassium ferrocyanide and 0.1% X-gluc (Clontech chemical) overnight. The stained plant materials were then cleared and fixed by rinsing with 100% and 70% ethanol successively, and the samples were examined and photographed directly or under a microscope. See FIG. 5.

The results of Southern blot analysis demonstrated that CoFS promoter/GUS gene was integrated into the tobacco genome. More than 50 tobacco transgenic plants were obtained and transplanted in soil to grow to maturation. Consistent with the results from Northern blot analysis of cotton, the GUS gene driven by the CoFS promoter was specifically and strongly expressed in tobacco anthers. Weak activity of GUS gene under CoFS promoter was also detected in ovaries, styles and stigmas, but no GUS activity was detected in petals or other tissues in all the transgenic tobacco plants studied. This result, together with the above Northern blot analysis, indicates that the CoFS promoter is able to control specific gene expression at the transcriptional level in plant anthers.

REFERENCES

Odell J T, Nagy F, Chua N-H, 1985. Identification of DNA sequences required for activity of the cauliflower mosaic virus 35S promoter. Nature, 313:810–2.

OW D W, Jacobs J D, Howell S H, 1987. Functional regions of the cauliflower mosaic virus 35S RNA promoter determined by use of the firefly luciferase gene as a reporter of promoter activity. Proc. Natl. Acad. Sci. USA, 84:4870–4.

McCabe D E and Martinell B J, 1993. Transformation of elite cotton cultivars via particle bombardment of meristems. Biotechnology, 11:596–8.

John M E, 1996. Structural characterization of genes corresponding to cotton fiber mRNA, E6: reduced E6 protein in transgenic plants by antisense gene. Plant Mol. Biol., 30(2):297–306.

Kawai M, Aotsuka S, Uchimiya H. 1998. Isolation of a cotton CAP gene: a homologue of adenylyl cyclase-associated protein highly expressed during fiber elongation. Plant Cell Physiol., 39(12):1380–3.

Song P and Allen R D, 1997. Identification of a cotton fiber-specific acyl carrier protein cDNA by differential display. Biochim. Biophys. Acta, 1351(1):305–12.

Ma dp, Liu H C, Tan H, Creech R G, Jenkins J N, Chang Y F, 1997. Cloning and characterization of a cotton lipid transfer protein gene specifically expressed in fiber cells. Biochim. Biophys. Acta, 1344(2):111–4.

Rinehart J A, Peterson M W, John M E, 1996. Tissue-specific and developmental regulation of cotton gene FbL2A. Demonstration of promoter activity in transgenic plants. Plant Physiol., 112(3):1331–41.

John M E and Crow L J, 1992. Gene expression in cotton fiber: cloning of the mRNAs. Proc. Natl. Acad. Sci. USA, 89(13):5769–73.

Jefferson R A, 1987. Assaying chimeric genes in plants: the GUS gene fusion system. Plant Mol. Biol. Rep., 5:387–405.

Jefferson R A, Kavanagh T A, Bevan M W, 1987. GUS fusion: -glucuronidase as a sensitive and versatile gene fusion marker in higher plants. EMBO J., 6:3901–7.

Loguerico L L, Zhang J Q, Wilkins T A, 1999. Differential regulation of six novel MYB-domain genes def two distinct expression patterns in allotetraploid cotton. Mol. Gen. Genet., 261 (4/5):660–71.

Hasenfratz M P, Tsou C L, Wilkins T A, 1995. Expression of two related vacuolar H(+)-ATPase 16-kilodalton proteolipid genes is differentially regulated in a tissue-specific manner. Plant Physiol., 108(4):1395–404.

John M E and Peterson M W, 1994. Cotton pollen-specific polygalacturonase mRNA: tissue and temporal specificity of its promoter in transgenic tobacco. Plant Mol. Biol., 26(6):1989–93.

Goldberg R, Beals T, Sanders P, 1993. Anther development: basic principles and practical applications. Plant Cell, 5: 1217–29.

Allen R L, Lonsdale D M, 1993. Molecular characterization of one of the maize polygalacturonase gene family members which are expressed during late pollen development. Plant J., 3:261–71.

Bird C R, Smith C J S, Ray J A, Moureau P, Bevan M W, Bird A S, Hughes S, Morris P C, Grierson D, Schuch W, 1988. The tomato polygalacturonase gene and ripening-specific expression in transgenic plants. Plant Mol. Biol., 11: 651–62.

Brown S M, Crouch M L, 1990. Characterization of a gene family abundantly expressed in Oenothera organensis pollen that shows sequence similarity to polygalacturonase. Plant Cell, 2: 263–74.

Grierson D, Tucker G A, Keen J, Ray J, Bird C R, Schuch W, 1986. Sequencing and identification of a cDNA clone for tomato polygalacturonase. Nucl. Acids Res., 14: 8595–603.

Hanson D D, Hamilton D A, Travis J L, Bashe D M, Mascarenhas J P, 1989. Characterization of a pollen-specific cDNA clone from Zea mays and its expression. Plant Cell, 1: 173–79.

Ursin V M, Yamaguchi J, McCormick S, 1989. Gametophytic and sporophytic expression of anther-specific genes in developing tomato anthers. Plant Cell, 1: 727–36.

Kamalay J C, Goldberg R B, 1984. Organ-specific nuclear RNAs in tobacco. Proc. Natl. Acad. Sci. USA, 81: 2801–5.

Koltunow A M, Truettner J, Cox K H, Wallroth M, Goldberg R B, 1990. Different temporal and spatial gene expression patterns occur during anther development. Plant Cell, 2: 1201–24.

Atanassov I, Russinova E, Antonov L, Atanassov A, 1998. Expression of an anther-specific chalcone synthase-like gene is correlated with uninucleate microspore development in Nicotiana sylvestris. Plant Mol. Biol., 38: 1169–78.

Liu J Q, Seul U, Thompson R, 1997. Cloning and characterization of a pollen-specific cDNA encoding a glutamic-acid-rich protein (GARP) from potato Solanum berthaultii. Plant Mol. Biol., 33: 291–300.

Treacy B K, Hattori J, Prud'homme I, Barbour E, Boutilier K, Baszczynski C L, Huang B, Johnson D A, Miki B L, 1997. Bnm1, a Brassica pollen-specific gene. Plant Mol. Biol., 34: 603–11.

Agnes F N, Drouaud J, Haouazine N, Pelletier G, Guerche P, 1999. Isolation of rapeseed genes expressed early and specifically during development of the male gametophyte. Plant Mol. Biol., 40: 857–72.

The invention claimed is:

1. An isolated promoter that is anther-specific comprising SEQ ID NO:2.

2. A transgenic plant expressing a transgene under control of a promoter of claim 1.

* * * * *